US012697245B2

(12) United States Patent　　　(10) Patent No.:　US 12,697,245 B2

Modelski　　　(45) Date of Patent:　　　Aug. 4, 2026

(54) PORTABLE, STANDALONE DEVICE FOR MUSCLE RECOVERY BY MEANS OF CRYOTHERAPY

(71) Applicant: Guillaume Modelski, Mauguio (FR)

(72) Inventor: Guillaume Modelski, Mauguio (FR)

( * ) Notice: Subject to any disclaimer, the term of this patent is extended or adjusted under 35 U.S.C. 154(b) by 328 days.

(21) Appl. No.: 18/557,296

(22) PCT Filed: Apr. 28, 2022

(86) PCT No.: PCT/EP2022/061401

§ 371 (c)(1),
(2) Date: Oct. 26, 2023

(87) PCT Pub. No.: WO2022/229348

PCT Pub. Date: Nov. 3, 2022

(65) Prior Publication Data

US 2024/0207087 A1　　Jun. 27, 2024

(30) Foreign Application Priority Data

Apr. 28, 2021　(FR) ...................................... 2104442

(51) Int. Cl.
*A61F 7/00*　　(2006.01)

(52) U.S. Cl.
CPC ........ *A61F 7/00* (2013.01); *A61F 2007/0029* (2013.01); *A61F 2007/0039* (2013.01); *A61F 2007/0057* (2013.01); *A61F 2007/0093* (2013.01)

(58) Field of Classification Search
CPC ...... A61F 2007/0029; A61F 2007/0039; A61F 2007/0052; A61F 2007/0057; A61F
2007/0063; A61F 2007/0064; A61F
2007/0093; A61F 2007/0096; A61F
2007/0225; A61F 2007/0228; A61F 7/00;
A61F 7/02; A61F 7/10
See application file for complete search history.

(56) References Cited

U.S. PATENT DOCUMENTS

| | | | |
|---|---|---|---|
| 5,449,379 A * | 9/1995 | Hadtke | .............. A61B 17/1325 |
| | | | 607/114 |
| 2020/0146880 A1* | 5/2020 | Jones | ......................... A61F 7/02 |
| 2021/0123641 A1* | 4/2021 | Monazami | .............. F25B 21/02 |

FOREIGN PATENT DOCUMENTS

| | | |
|---|---|---|
| WO | 0168185 A1 | 9/2001 |
| WO | 2019023569 A1 | 1/2019 |

OTHER PUBLICATIONS

ISR; European Patent Office; NL; Jul. 20, 2022.

* cited by examiner

*Primary Examiner* — Tigist S Demie

(74) *Attorney, Agent, or Firm* — Patshegen IP; Moshe Pinchas

(57) ABSTRACT

The standalone mobile device (10) for muscle recovery by cryotherapy comprises:

a container (11) of pressurised fluid;

an expander (12) for reducing the pressure of the pressurised fluid, fluidically connected to the container and equipped with an outlet (20) for the expanded gas;

a sheet (13) of thermally conductive material configured to rest on the skin of the user, and equipped with a heat exchanger radiator (14) positioned on the path of the expanded gas output from the gas expander.

16 Claims, 8 Drawing Sheets

PORTABLE, STANDALONE DEVICE FOR MUSCLE RECOVERY BY MEANS OF CRYOTHERAPY

TECHNICAL FIELD OF THE INVENTION

The present invention relates to a standalone mobile device and a method for muscle recovery by cryotherapy. It applies, in particular, to recovery with an intense muscular effort, typically sports-related, and to the reduction of muscle pains and oedemas, whatever their cause. More specifically, the invention relates to muscle recovery for the different limbs of the body, in particular calves and thighs.

STATE OF THE ART

During an intense physical effort by the body, the muscles consume more oxygen than the arteries are supplying to these muscles. In effect, the muscular effort reduces the venous pressure and the repeated muscle contractions compress the intramuscular feeding vessels, which reduces the supply of blood and oxygen.

This leads to toxins accumulating in the muscles, which the body will try to eliminate by increasing the circulation of fluids through an inflammatory response. This results in muscle fatigue, aches and pains.

In this context, the beneficial nature of cryotherapy is known, in particular for muscle recovery after making a significant physical effort.

However, to observe a beneficial effect of cryotherapy on muscle recovery it is necessary to create a thermal shock at the skin surface of the anatomical area that one wishes to treat. Such a thermal shock is obtained when the skin temperature is reduced to a temperature below or equal to 0° C. However, cryotherapy entails going to an establishment having the necessary equipment, which imposes a significant delay between the muscular effort and the cryotherapy effect, and a consequential loss of time.

Socks are also known that, in the portion around the foot, comprise pockets into which gel pads can be placed which, as required, can be heated or cooled depending on whether one wants to warm the feet or, on the contrary, cool them, and thus alleviate a temporary or chronic pain. Such a sock, as it only extends around the foot, cannot contribute to the muscle recovery of a user's leg, especially the calf. In addition, this sock is limited to acting on the foot by supplying heat or cold through pads that are themselves cooled or heated by external means, which therefore have to be obtained. These socks are therefore not standalone.

Document US 2016/0051400 is also known, which describes a boot likely to contain a cold liquid, in particular iced water. The sportsperson is therefore able to put such a boot on immediately at the end of physical exercise to start the muscle recovery process. However, this boot has a number of drawbacks. The use of iced water does not allow a sufficient thermal shock to be created to be able to observe significant physiological benefits. Additionally, it is necessary to provide external means for cooling the water. Consequently, these boots are not standalone.

This boot also comprises means for circulating the cold fluid around the foot, these means often consisting, in particular, of an air pump. In addition, it scarcely offers the possibility of precisely targeting the areas of the leg to be cooled.

Patent application WO2019/023569 is known, which discloses a device for cryoablation, i.e. tissue destruction. Patent application WO01/68185 is also known, which discloses a device for vascular laser treatment having a cooled surface to avoid burning a user's skin, through which a vein is treated.

Obviously, these documents are very different from the invention since they do not concern a muscle recovery device in any way.

DESCRIPTION OF THE INVENTION

The present invention aims to remedy all or part of these drawbacks.

To this end, according to a first aspect, the present invention aims at a standalone mobile device for muscle recovery by cryotherapy, which comprises:

a container of pressurised fluid;
an expander for reducing the pressure of the pressurised fluid, fluidically connected to the container and equipped with an outlet for the expanded gas;
a sheet of thermally conductive material configured to rest on the skin of the user, and equipped with a heat exchanger radiator positioned on the path of the expanded gas output from the fluid expander.

The expansion of the fluid cause significant cooling of the expanded gas leaving the expander, this gas being warmed on contact with the radiator and cooling the radiator and the sheet resting on the skin of the user. The device that is the subject of the invention requires no external means to work, and can have similar dimensions and weight to a bottle of water. It is therefore mobile and easily transportable.

In some embodiments, the device also comprises a removable support means for keeping the sheet in position against a user's limb.

Thanks to these provisions, the device can be kept in place with regard to a user's muscle without effort by the user.

In some embodiments, the removable support means comprises at least one strip of hook-and-loop fabric.

Thanks to these provisions, the user does not have to carry out a complicated operation.

In some embodiments, the device also comprises a means for controlling the passage of fluid between the container and the expander, the control means being configured to limit, during use, the average flow rate of fluid leaving the container to a value lower than the maximum possible flow rate.

Thanks to these provisions, the risks of excessive cooling, which could result in "burning" of the user's skin, are avoided.

In some embodiments, the device comprises at least one sensor of a temperature representative of the sheet in contact with the skin, the control means being configured to servo the flow rate of fluid leaving the container to the temperature captured.

In this way, one controls the temperature applied to the user's skin, regardless of the outside temperature, and, possibly, a predefined gradual cooling curve to regulate this temperature applied to the skin.

In some embodiments, the container comprises a valve which opens by angular offset, the control means comprising a servomotor resting on the expander and the control means being configured to control the movement of the servomotor.

In some embodiments, the container comprises a valve which opens by translation towards the container, the control means comprising a servomotor resting on the expander and the control means being configured to control the movement of the servomotor.

In some embodiments, the sheet of thermally conductive material comprises aluminium.

In some embodiments, the sheet of thermally conductive material has a concave shape.

In some embodiments, the pressurised fluid in the container is hydrofluoroolefin in the form of a compressed gas.

HFOs (HydroFluoroOlefins) are fourth-generation refrigerants. They provide low-GWP alternatives that reduce the environmental impact while offering energy efficiency.

According to a second aspect, the invention aims at a mechanical connector for a device that is the subject of the invention, configured to keep a container of pressurised fluid in position in a compartment of the device such that the expander is fluidically connected to the container.

In some embodiments, the mechanical connector has a general cylindrical shape with a circular guide, a central opening and radial spurs extending beyond the generatrix of this cylindrical shape.

In some embodiments, the mechanical connector has portions of spheres on the inner surface of the opening.

In some embodiments, the mechanical connector comprises radial indentations in its cylindrical wall, which indentations define clips having retractable tabs oriented towards the central axis of the connector, and which indentations' free end has a chamfered shape.

As the particular features, advantages and aims of this mechanical connector are similar to those of the device that is the subject of the invention, they are not repeated here.

According to a third aspect, this invention aims at a method for muscle recovery by cryotherapy, which comprises:

a step of positioning a sheet of thermally conductive material configured to rest on the skin of the user, and equipped with a heat exchanger radiator;

a step of expanding a pressurised fluid against the sheet.

In some embodiments, the method that is the subject of the present invention also comprises:

a step of measuring the temperature of the sheet;

a step of comparing the temperature measured to a predefined temperature limit, in which method the expansion step is utilised depending on the result of the comparison step.

As the particular features, advantages and aims of the method that is the subject of the present invention are similar to those of the device that is the subject of the invention, they are not repeated here.

BRIEF DESCRIPTION OF THE FIGURES

Other advantages, aims and particular features of the invention will become apparent from the non-limiting description that follows of at least one particular embodiment of the device, method and kits that are the subjects of the present invention, with reference to drawings included in an appendix, wherein.

DESCRIPTION OF THE EMBODIMENTS

The present description is given in a non-limiting way, in which each characteristic of an embodiment can be combined with any other characteristic of any other embodiment in an advantageous way.

Figure 1:
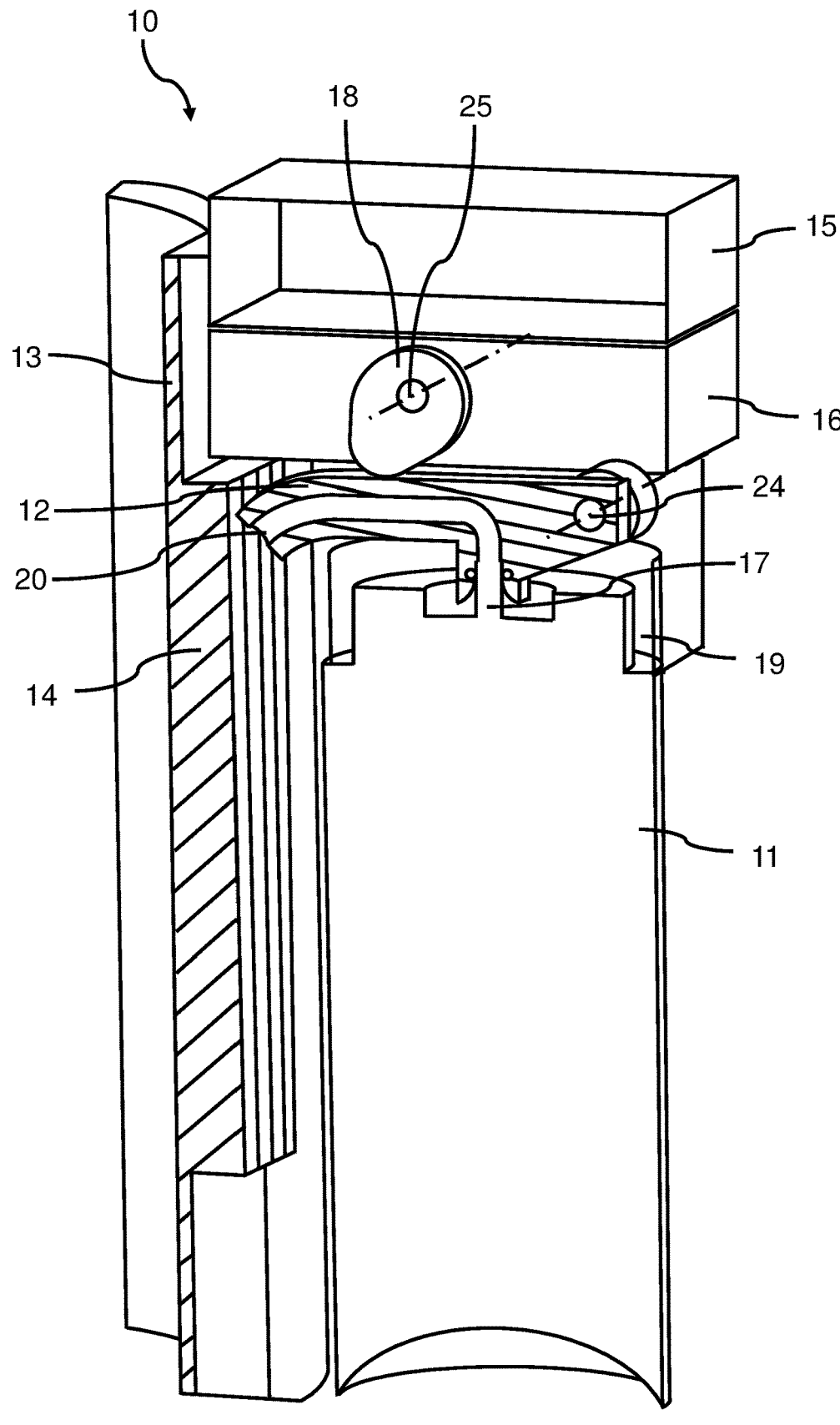
FIG. 1 represents, schematically, in perspective and in cross-section, a first particular embodiment of the device.
Figure 2:
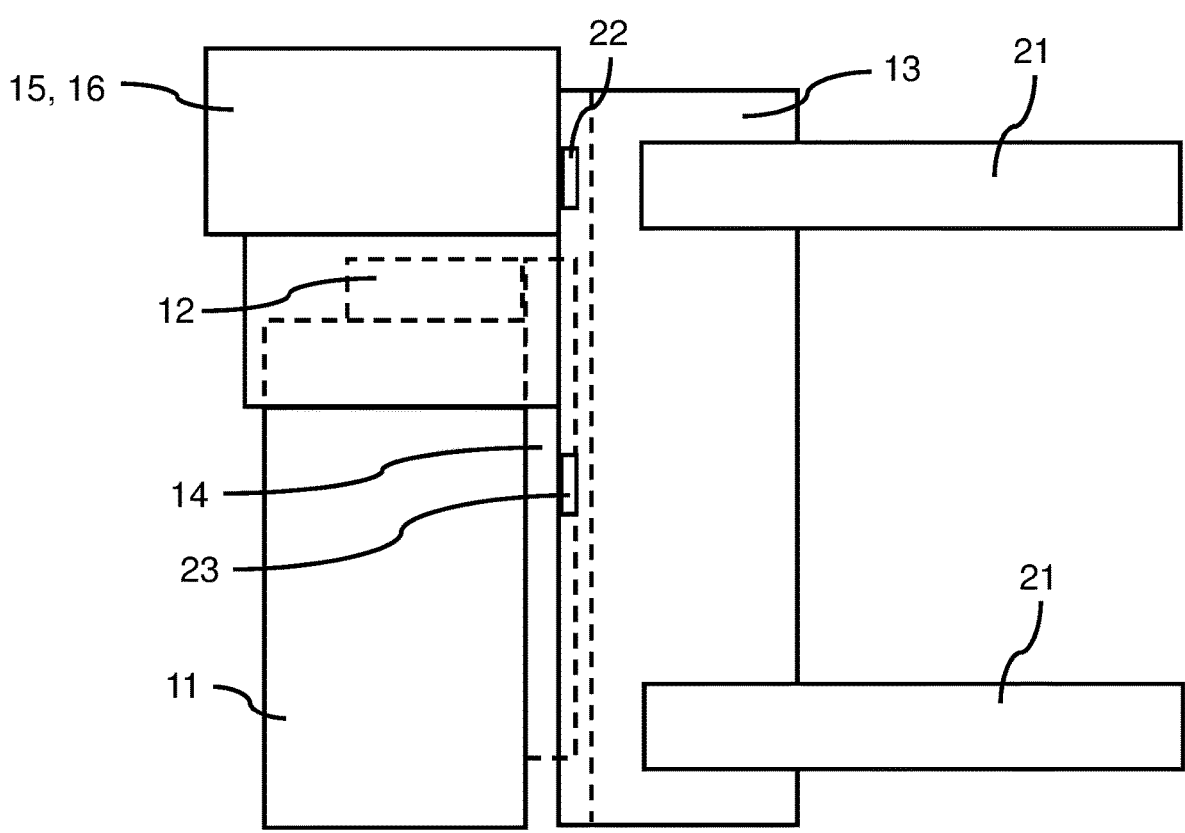
FIG. 2, represents, schematically in a side view, the device illustrated in FIG. 1.

Throughout the description, the term "upper" or "top" refers to being located at the top in FIGS. 1 and 2, and "bottom" or "lower" to being located at the bottom in these figures. FIGS. 1 and 2 show the orientation of the device during use. The "heights" flow from these definitions. The "widths" are defined from top to bottom in FIG. 3, which represents a top view of the device. The term "inner" or "inside" refers to being located close to or facing the container of pressurised fluid, and "outer" or "outside" refers to being located farther away from this container or facing the outside of the device.

Note that FIGS. 6 to 11 are to scale, but the other figures are not to scale.

Figure 3:
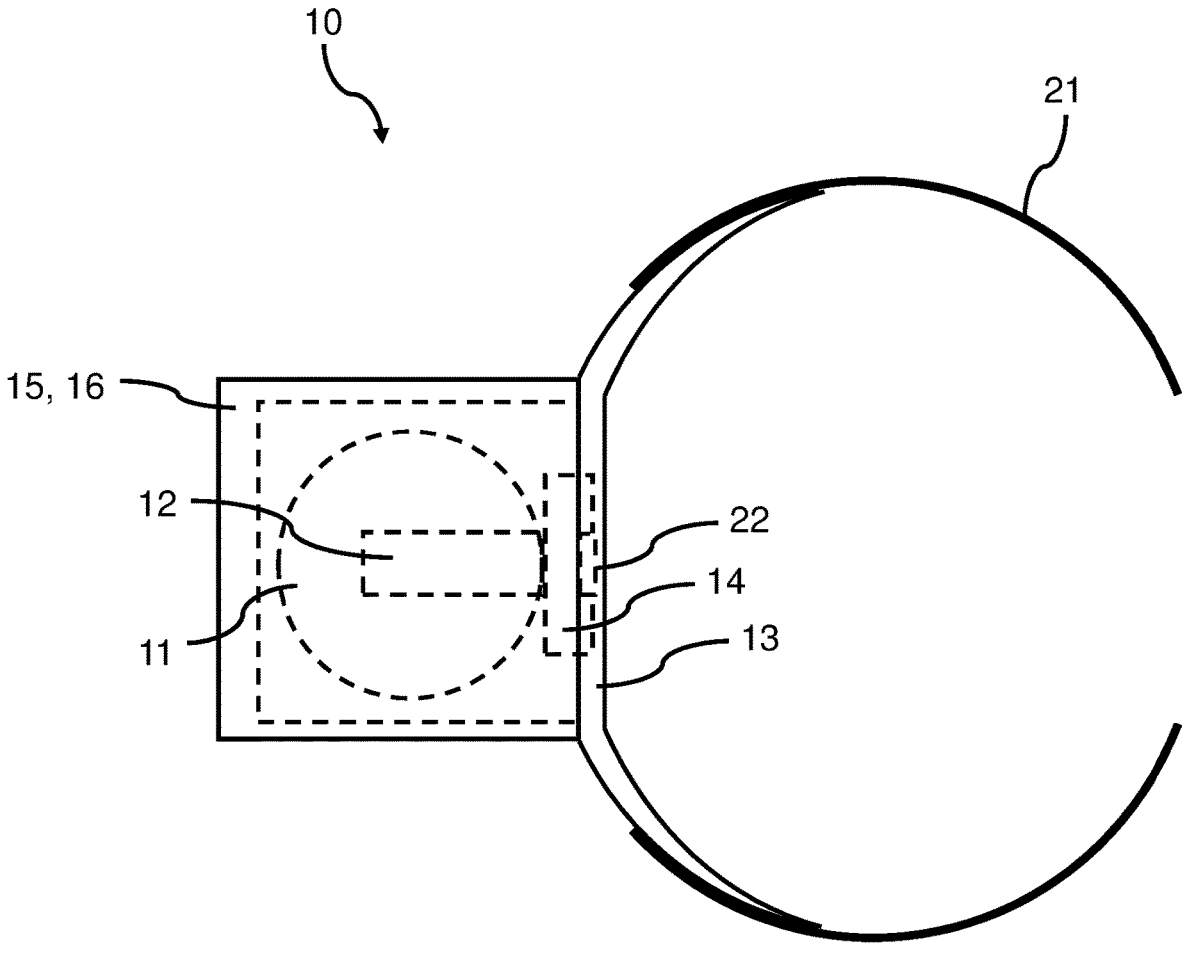
FIG. 3, represents, schematically, in a top view, the device illustrated in FIG. 1.

FIGS. 1 to 3 show a particular embodiment 10 of the standalone mobile device for muscle recovery by cryotherapy that is the subject of the invention. The device 10 comprises, preferably in a manually removable manner without breakage of any part, a container 11 of pressurised fluid. This fluid can be a liquid. However, this fluid is preferably a pressurised gas. More preferably, the pressurised gas in the container 11 is hydrofluoroolefin ("HFO").

The device 10 also comprises an expander 12 for reducing the pressure of the pressurised fluid, fluidically connected to the container 11 and equipped with an outlet 20 for the expanded gas. Because of the laws of thermodynamics, the expanded gas is much colder than the fluid in the container 11.

The device 10 further comprises a sheet 13 of thermally conductive material configured to rest on the skin of the user, and equipped with a heat exchanger radiator 14 positioned on the path of the expanded gas output from the fluid expander 12. The radiator 14 has, for example, parallel vertical metal fins between which the expanded gas from the outlet 20 of the expander 12 circulates.

The very cold gas leaving by the outlet 20 of the expander 12 is warmed on contact with the radiator 14 and cools the radiator 14 and the sheet 13 resting on the skin of the user. The sheet 13 can therefore have a temperature lower than or equal to 0° C. The device 10 requires no external means to work, and can have similar dimensions and weight to a bottle of water. It is therefore mobile and easily transportable.

In some embodiments (not shown), the user can actuate the expander 12 himself to cause the cooling of the sheet 13. However, such an operation could be dangerous, since temperatures that are too low can result in "burning" of the skin.

In the embodiment shown in FIGS. 1 to 3, the device 10 comprises a means 16 for controlling the passage of fluid between the container 11 and the expander 12. The control means 16, preferably having a controller and program memory, is configured to limit, during use, the average flow rate of fluid leaving the container 11 to a value lower than the maximum possible flow rate. A battery 15 electrically powers the control means 16.

To control the flow rate of the expanded fluid at the outlet 20 of the expander 12, the control means 16 controls the opening of the valve 17 of the container 11. In the device 10, the container 11 comprises a valve 17 which opens by angular offset, and the control means 16 comprises a servomotor 18 resting on the expander 12. The expander 12 is rotatably moveable around an axis 24 and the rectangular cam of the servomotor 18 is rotatably moveable around an axis 25. The control means 16 is configured to control the movement of the servomotor 18.

In some embodiments (not shown), the container comprises a valve which opens by translation towards the container, the control means comprising a servomotor resting on the expander. The control means is therefore also configured to control the movement of the servomotor.

Preferably, the device 10 comprises at least one sensor 22 or 23 of a temperature representative of the sheet 13 in contact with the skin. In this case, the control means 16 is configured to servo the flow rate of fluid at the outlet 20 of the expander 13 to at least one captured temperature. In this way, one controls the temperature applied by the sheet 13 to the user's skin, regardless of the outside temperature, and, possibly, a predefined gradual cooling curve (see FIG. 4) to regulate this temperature applied to the skin. Preferably, at least two temperature sensors, for example thermistors, are positioned at different places in the sheet 13. In the figures, the temperature sensor 22 is positioned close to one end of the sheet 13 and the temperature sensor 23 is positioned at the centre of the sheet 13.

A mechanical connector or adapter 50 (see FIGS. 6 to 12), in a receptacle 19, keeps the valve 17 of the container 11 in place relative to the expander 12, in a manually removable manner without breakage of any part. This mechanical connector 50 is preferably made of a thermally insulating material.

To keep the device 10 on a limb of the user, and more specifically against the muscles of his body, the device 10 comprises at least one support means for keeping the sheet in position against a user's limb. Preferably, the support means comprises at least one belt 21 (not shown in FIG. 1), preferably a strip of hook-and-loop fabric, commonly called "Velcro®". In some embodiments, the support means comprises a strip of adhesive tape. In some embodiments, the support means comprises a strap equipped with a tightening loop, a retractable latch or a retractable stop.

The support means is configured to keep the sheet in contact with a user's skin, at the location of at least one muscle of the user. Preferably, the support means is configured to enclose a limb of the user, i.e. the support means and at least one portion of the sheet wrap around the user's limb.

In some embodiments, the sheet 13 of thermally conductive material comprises aluminium. In some embodiments, the sheet 13 of thermally conductive material has a concave shape, shown in FIGS. 1 and 3. This concave shape, here cylindrical with a vertical axis, adopts the shape of a limb of the user and increases the transmission of negative heat from the sheet 13 to the limb considered.

Note that the device that is the subject of the invention can be used in cryotherapy mode and/or in cryotherapy and compression mode thanks to at least one compression textile, for example the compression textile for sportspersons.

According to one aspect, the invention relates to a kit element for muscle recovery by cryotherapy, which comprises an expander for reducing the pressure of the pressurised fluid equipped with an outlet for the expanded gas mechanically connected to a sheet of thermally conductive material configured to rest on the skin of the user, and equipped with a heat exchanger radiator positioned on the path of the expanded gas output from the fluid expander, and a mechanical connector configured to keep a container of pressurised fluid in position in a compartment such that the expander is fluidically connected to the container.

Figure 4:
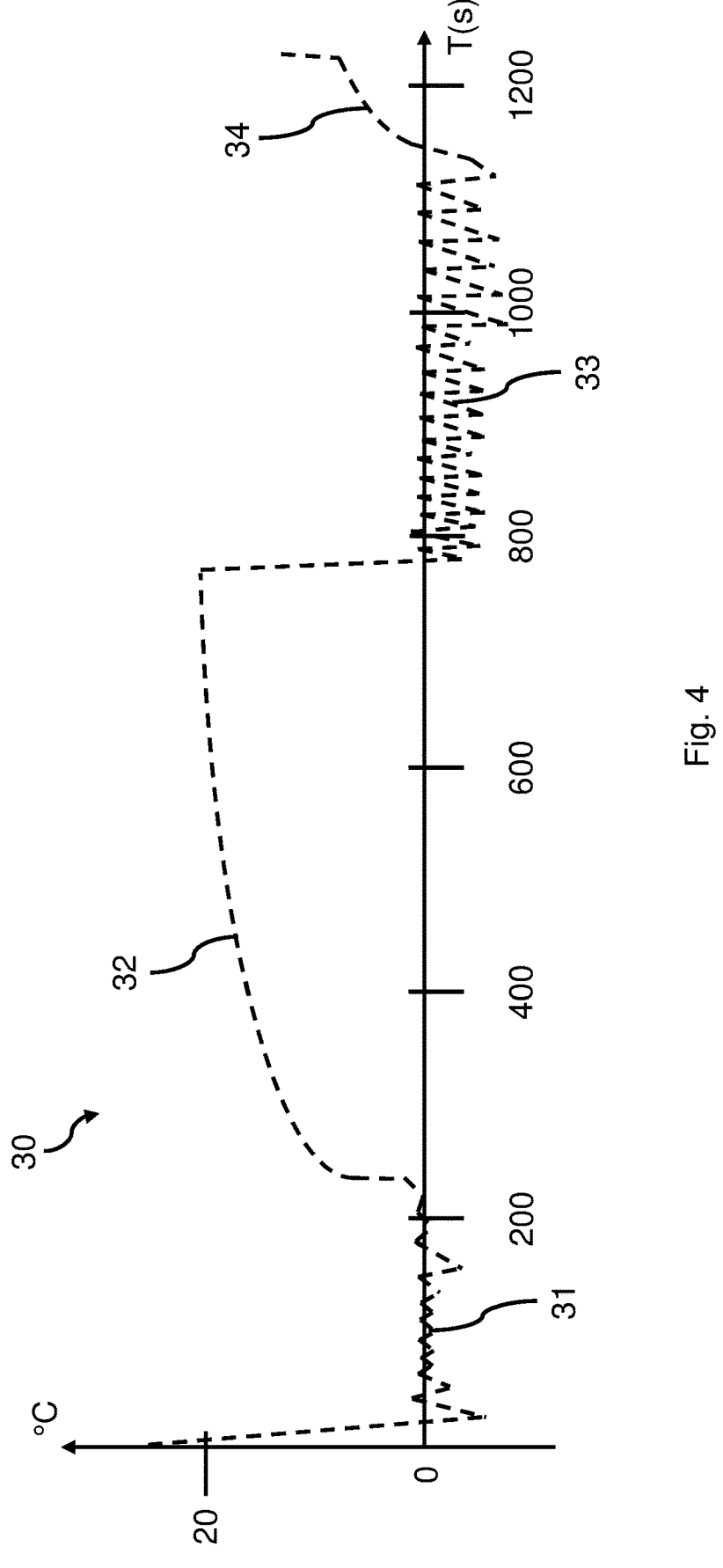
FIG. 4 represents, schematically, a temperature curve observed with a device that is the subject of the invention.

FIG. 4 shows the sequence of a 21-minute session of muscle recovery by cryotherapy. The x-axis shows the temperature measured by a temperature sensor, for example the sensor 23, in degrees Celsius. The y-axis shows time, in seconds. The curve 30 of temperature as a function of time comprises a first sequence 31, extending from time 0 to about 230 seconds including about 180 seconds with a temperature fluctuating around 0° C., after an initial sharp drop in temperature ordered by the control means 16 until the temperature measured is lower than or equal to 0° C. The control means 16 then triggers a pulse of gas expansion each time the temperature measured is above 0° C. The inventor has observed that these pulses follow substantially every 20 seconds. During a second sequence 32, extending substantially from second 230 to second 780, no gas expansion is ordered by the control means 16. The third sequence 33 is similar to the first sequence 31, except that it extends substantially from second 780 to second 1140. During the last sequence 34, no gas expansion is ordered by the control means 16.

For a temperature of the container 11 of 15° C. and an ambient temperature of 19° C., a calf temperature of 31° C. was observed at the beginning of the session and a temperature of 15° C. at the end of the session, the user experiencing a sensation of local anaesthesia. This recovery session uses about 90 grammes of compressed gas.

Figure 5:
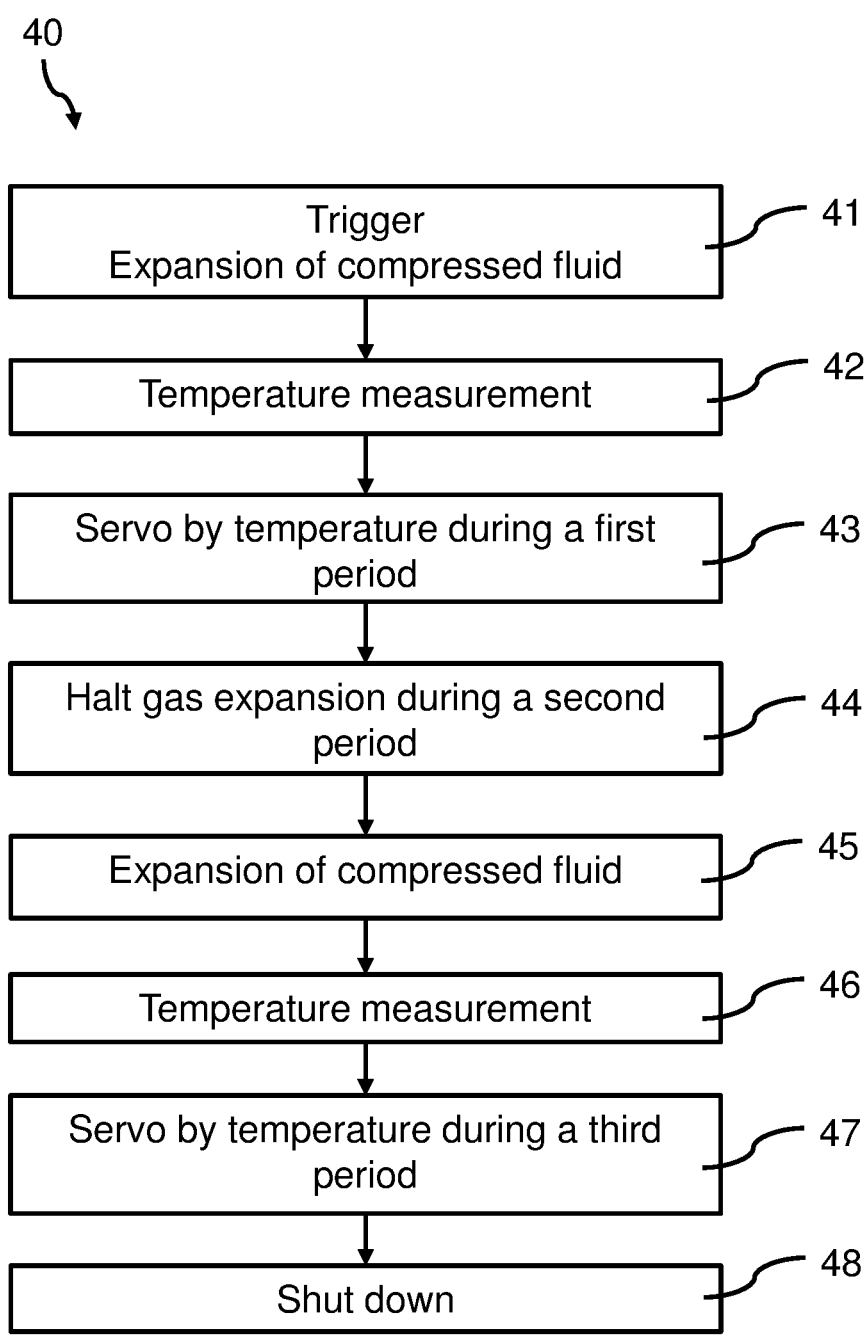
FIG. 5 represents, in the form of a logic diagram, steps in a particular embodiment of the method that is the subject of the invention.
Figures 6, 7:
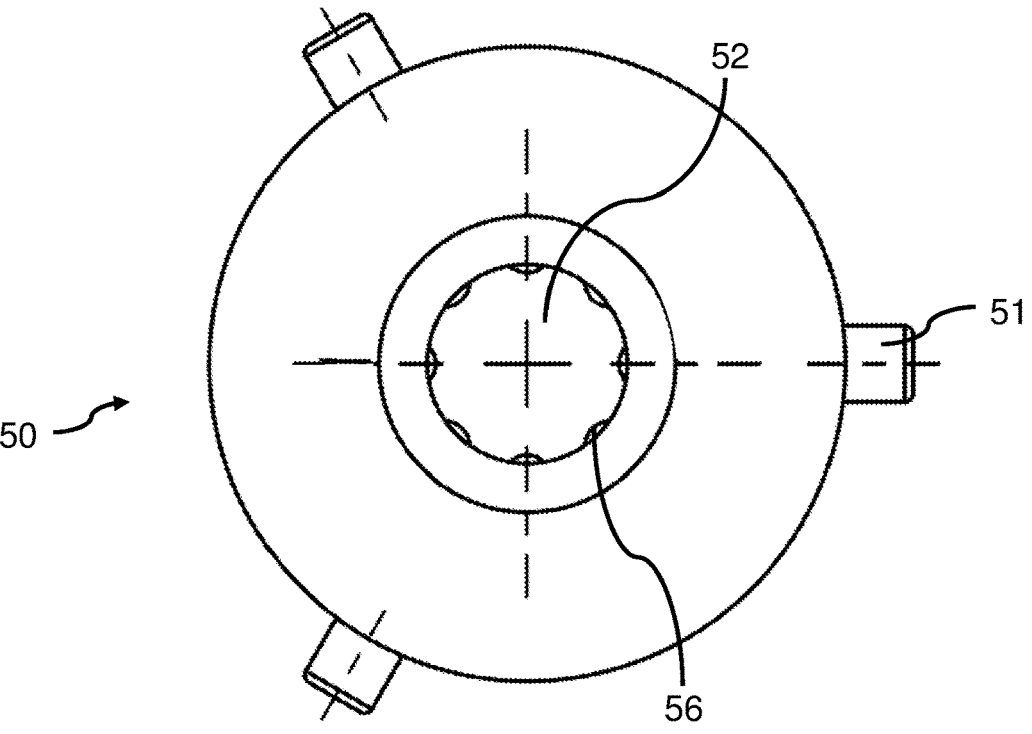
FIG. 6 represents, schematically, in a bottom view, a container adapter on the device that is the subject of this invention.
FIG. 7, represents, in a top view, the adapter illustrated in FIG. 6.
Figure 8:
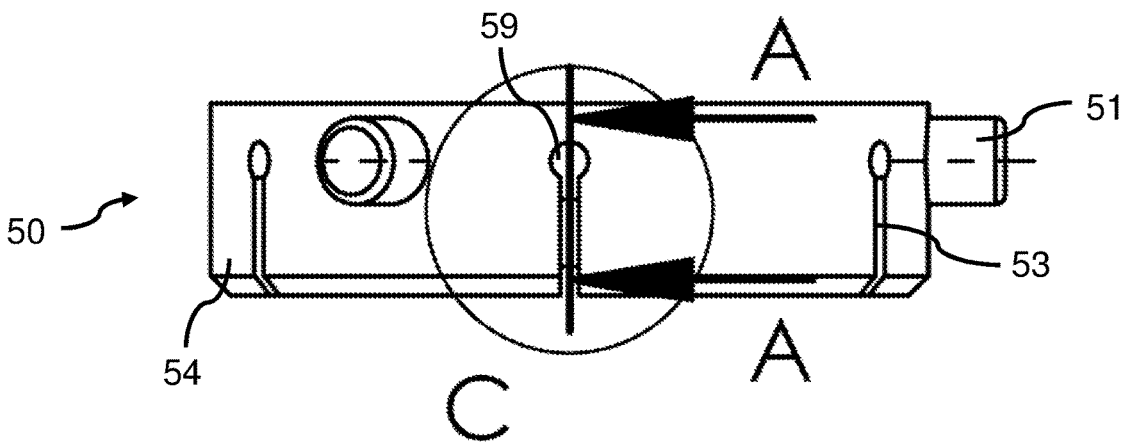
FIG. 8 represents, in a side view, the adapter illustrated in FIGS. 6 and 7.
Figure 9:
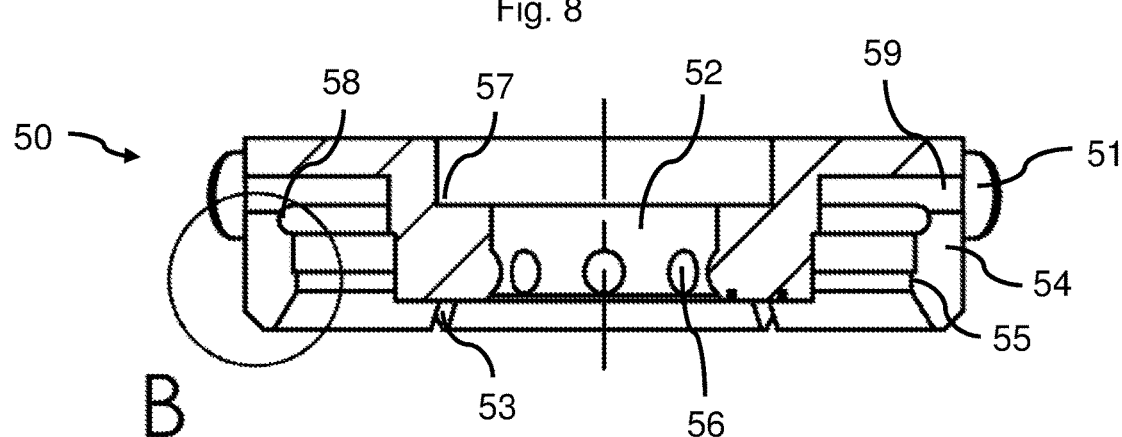
FIG. 9 represents a top view, along a cross-section A-A shown in FIGS. 6 and 8, of the adapter illustrated in FIGS. 6 to 8.

FIG. 5 shows the steps of an operation 40 of the device that is the subject of the invention. During a step 41 the user, after positioning the sheet 13 against his muscle to be treated, and possibly tightening the support means, initiates the operation of the device and, in particular, the supply of electricity to the control means 16 by the battery 15. This control means 16 triggers the expansion of gas through the expander 12.

During steps 42 and 43, the temperature of the sheet 13 is monitored continuously. During step 43 and for a first period (about 230 seconds in FIG. 4), the control means 16 servos the opening of the valve 17, by means of the servomotor 18, to the temperature measured. Once the temperature becomes lower than or equal to 0° C., the control means 16 halts the gas expansion, and once the temperature becomes higher than or equal to 0° C., the control means 16 triggers a pulse of gas expansion.

During a step 44, at the end of the first period, the control means halts the gas expansion during a second period (about 550 seconds in FIG. 4).

During a step 45 after the end of step 44, the control means 16 triggers the expansion of gas. The temperature is measured continuously during steps 46 and 47. During step 47 and for a first period (about 360 seconds in FIG. 4), the control means 16 servos the opening of the valve 17, by means of the servomotor 18, to the temperature measured. Once the temperature becomes lower than 0° C., the control means 16 halts the gas expansion, and once the temperature becomes higher than 0° C., the control means 16 triggers a pulse of gas expansion.

Lastly, the device 10 is shut down during a step 48.

The present invention has the following advantages:
a continuous operation for at least 10 minutes with a full container of 100 mL;
a possible operation with different container formats that can range from 100 mL to 600 mL;
an anaesthetic effect.

FIGS. 6 to 12 show an adapter 50 positioned as a mechanical interface between the container 11 and the device 10. The mechanical connector 50 for a device 10 that is the subject of the invention, is configured to keep a container 11 of pressurised fluid in position in a compartment 19 of the device 10 such that the expander is fluidically connected to the container. The adapter 50 is made of a plastic material, for example ABS (acrylonitrile-butadiene-styrene) or PA (polyamide).

The adapter 50 has a general cylindrical shape with a circular base, between two planes perpendicular to the generatrices, whose distance is of the order of half the radius of the cylindrical shape of the adapter 50. This shape comprises external projections 51 and recesses.

The radial projections 51 extend perpendicular to the generatrix (vertical in FIGS. 8 and 9) and extend beyond the generatrix of this cylindrical shape. These projections or spurs 51, preferably cylindrical and three in number, are involved in a bayonet movement: translational guidance and then rotational guidance of the adapter 50 in slots or grooves (not shown) of the body of the device 10, screwing the head of the container 11 into the body of the device 10 to put the nozzle 17 of the container 11 at the correct height, relative to the gas release nozzle or expander 12, immobilising the head of the container 11 in the body of the device 10.

A central through-opening 52 allows the passage of the nozzle 17 of the container 11 from the body of the container 11 through to the gas release nozzle of the expander 12. The central opening 52 has a shoulder 57. Portions of spheres 56, present on the inner cylindrical surface of the opening 52, serve as obstructions in the deformations of the crimping of the valve of the container 11 and/or to prevent the rotation of the adapter 50 on the container 11.

Figure 11:
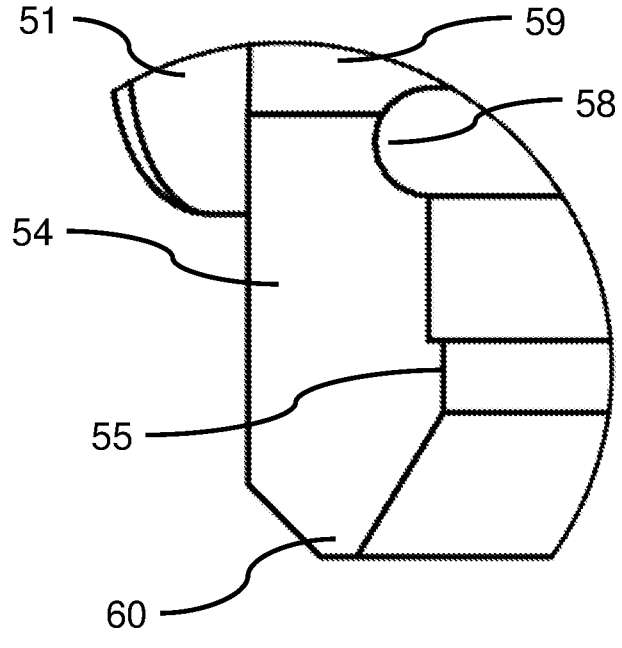
FIG. 11 represents a detailed view labelled B in FIG. 9.
Figure 12:
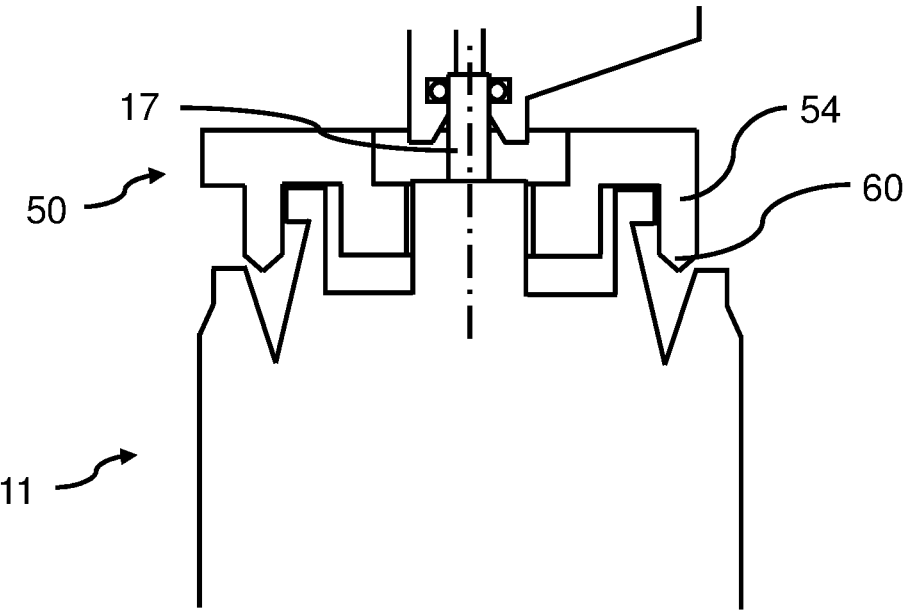
FIG. 12 represents, schematically, an adapter that is the subject of the invention in a partial view of the container and the device that is the subject of the invention.

Radial indentations 53 (here six in number) allow the lateral deformation of clips 54 of the adapter 50 formed by the periphery of the adapter 50 between the indentations 53. These clips 54, whose cross-section is shown in FIG. 11, have:
grooves 58 corresponding to the upper crimping of the body of the container 11; and
retractable tabs 55 that enclose the head of the container 11 and mechanically retain the container 11 in the device 10. These retractable tabs 55 are oriented towards the central axis of the connector 50.

Figure 10:
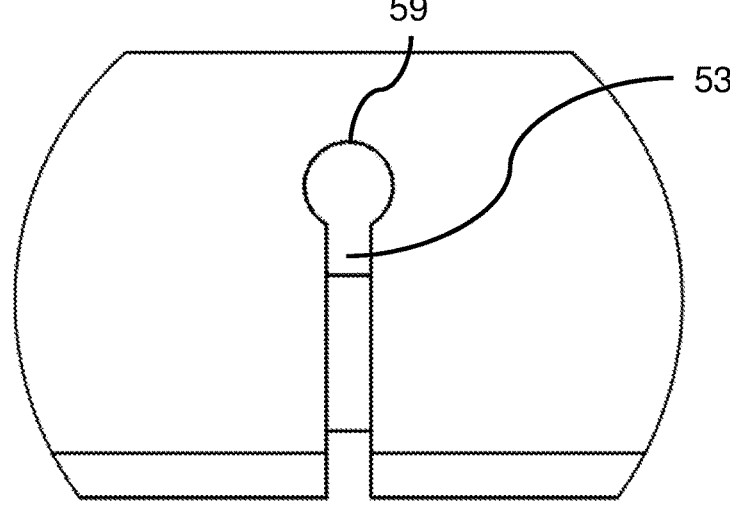
FIG. 10 represents a detailed view labelled C in FIG. 8.

The indentations 53 preferably have a rounded end 59 to prevent stress concentrations, as shown in FIG. 10. The clips 54 have a free end 60 with a chamfered shape giving them a triangular cross-section, to facilitate the penetration of the clips 54 into the upper relief of the container 11.

The invention claimed is:

1. Standalone mobile device for muscle recovery by cryotherapy, characterised in that it comprises:
a container of pressurised fluid;
an expander for reducing the pressure of the pressurised fluid, fluidically connected to the container and equipped with an outlet for the expanded gas;

a sheet of thermally conductive material configured to rest on a skin of a user, and equipped with a heat exchanger radiator positioned on a path of the expanded gas output from the gas expander, the radiator having parallel vertical metal fins between which the expanded gas from the outlet of the expander circulates.

2. Device according to claim 1, which also comprises a removable support means for keeping the sheet in position against a user's limb.

3. Device according to claim 2, wherein the removable support means comprises at least one strip of hook-and-loop fabric.

4. Device according to claim 1 which also comprises a means for controlling the passage of fluid between the container and the expander, the control means being configured to limit, during use, an average flow rate of fluid leaving the container to a value lower than a maximum possible flow rate.

5. Device according to claim 4, which also comprises at least one sensor of a temperature representative of the sheet in contact with the skin, the control means being configured to servo the flow rate of fluid leaving the container to a temperature captured.

6. Device according to claim 4, wherein the container comprises a valve which opens by angular offset, the control means comprising a servomotor resting on the expander and the control means being configured to control a movement of the servomotor.

7. Device according to claim 4, wherein the container comprises a valve which opens by translation towards the container, the control means comprising a servomotor resting on the expander and the control means being configured to control a movement of the servomotor.

8. Device according to claim 1, wherein the sheet of thermally conductive material comprises aluminum.

9. Device according to claim 1, wherein the sheet of thermally conductive material has a concave shape.

10. Device according to claim 1, wherein the pressurised fluid in the container is hydrofluoroolefin in the form of a compressed gas.

11. Mechanical connector for a device according to claim 1, configured to keep the container of pressurised fluid in position in a compartment of the device such that the expander is fluidically connected to the container.

12. Mechanical connector according to claim 11, which has a general cylindrical shape with a circular guide, a central opening and radial spurs extending beyond a generatrix of this cylindrical shape.

13. Mechanical connector according to claim 12, which has portions of spheres on an inner surface of the opening.

14. Mechanical connector according to claim 11, which comprises radial indentations in its cylindrical wall, which indentations define clips having retractable tabs (55) oriented towards a central axis of the connector, and which indentations' free end has a chamfered shape.

15. Method for muscle recovery by cryotherapy, characterised in that it comprises:
a step of positioning a sheet of thermally conductive material configured to rest on the skin of the user, and equipped with a heat exchanger radiator,
a step of expanding a pressurised fluid against the sheet, wherein the radiator has parallel vertical metal fins between which the expanded gas from an outlet of the expander circulates.

16. Method according to claim 15, which also comprises:
a step of measuring a temperature of the sheet;

a step of comparing the temperature measured to a predefined temperature limit, in which method the expansion step is utilised depending on the result of the comparison step.

* * * * *